(12) United States Patent
Rao

(10) Patent No.: US 10,390,972 B2
(45) Date of Patent: Aug. 27, 2019

(54) HUMERAL TRIAL ADAPTOR

(71) Applicant: Howmedica Osteonics Corp., Mahwah, NJ (US)

(72) Inventor: Koustubh Rao, Hackensack, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 108 days.

(21) Appl. No.: 14/997,128

(22) Filed: Jan. 15, 2016

(65) Prior Publication Data

US 2017/0202685 A1 Jul. 20, 2017

(51) Int. Cl.
| | |
|---|---|
| *A61F 2/40* | (2006.01) |
| *A61B 17/00* | (2006.01) |
| *A61B 17/84* | (2006.01) |
| *A61F 2/46* | (2006.01) |
| *A61F 2/30* | (2006.01) |

(52) U.S. Cl.
CPC .......... *A61F 2/4684* (2013.01); *A61F 2/4014* (2013.01); *A61B 17/842* (2013.01); *A61B 2017/00707* (2013.01); *A61F 2/4059* (2013.01); *A61F 2002/30331* (2013.01); *A61F 2002/30451* (2013.01); *A61F 2002/30579* (2013.01); *A61F 2002/30594* (2013.01); *A61F 2002/4022* (2013.01); *A61F 2002/4051* (2013.01); *A61F 2220/0033* (2013.01)

(58) Field of Classification Search
CPC ............ A61F 2/4684; A61F 2/40–4081; A61F 2/4648; A61B 2017/00707
See application file for complete search history.

(56) References Cited

U.S. PATENT DOCUMENTS

| | | |
|---|---|---|
| 3,102,536 A | 9/1963 | Rose |
| 3,806,957 A | 4/1974 | Shersher et al. |

(Continued)

FOREIGN PATENT DOCUMENTS

| | | |
|---|---|---|
| DE | 10335442 A1 | 2/2005 |
| DE | 202008008565 U1 | 8/2008 |

(Continued)

OTHER PUBLICATIONS

BIOMET, Comprehensive Reverse Shoulder System / Surgical Technique, Copyright 2014, 49 pages.
(Continued)

*Primary Examiner* — Marcia L Watkins
(74) *Attorney, Agent, or Firm* — Lerner, David, Littenberg, Krumholz & Mentlik, LLP

(57) ABSTRACT

Orthopedic trialing systems include a stem, an adaptor and a trial member. The stem may be a trial or implant stem. The trial member may be a cup or head. The adaptor is used to account for the difference in the coupling of the trial member and stem and an implant member and stem. The stem has a first coupling feature and a shaft portion adapted to be received in a canal of a bone of a patient. The adaptor has planar top and bottom surfaces and at least one aperture therethrough. The trial member has a second coupling feature, wherein one of the first and second coupling features of either the trial member or stem extends through the aperture of the adaptor and at least partially into the other of the first and second coupling features for coupling together the trial member, the adaptor and the stem.

11 Claims, 11 Drawing Sheets

(56) References Cited

U.S. PATENT DOCUMENTS

| | | |
|---|---|---|
| 3,978,528 A | 9/1976 | Crep |
| 4,030,143 A | 6/1977 | Elloy et al. |
| 4,040,131 A | 8/1977 | Gristina |
| 4,279,041 A | 7/1981 | Buchholz et al. |
| 4,524,467 A | 6/1985 | DeCarlo, Jr. |
| 4,693,723 A | 9/1987 | Gabard et al. |
| 5,358,526 A | 10/1994 | Tornier |
| 5,462,563 A | 10/1995 | Shearer et al. |
| 5,489,309 A | 2/1996 | Lackey et al. |
| 5,569,263 A | 10/1996 | Hein |
| 5,609,639 A | 3/1997 | Walker et al. |
| 5,609,644 A | 3/1997 | Ashby et al. |
| 5,658,340 A | 8/1997 | Muller et al. |
| 5,702,457 A | 12/1997 | Walch et al. |
| 5,702,470 A | 12/1997 | Menon |
| 5,702,486 A | 12/1997 | Craig et al. |
| 5,723,018 A | 3/1998 | Cyprien et al. |
| 5,728,161 A | 3/1998 | Camino et al. |
| 5,741,335 A | 4/1998 | Gerber et al. |
| 5,755,801 A | 5/1998 | Walker et al. |
| 5,800,556 A | 9/1998 | Sanders et al. |
| 5,824,106 A | 10/1998 | Fournol |
| 5,879,401 A | 3/1999 | Besemer et al. |
| 5,961,555 A | 10/1999 | Huebner |
| 6,015,437 A | 1/2000 | Stossel |
| 6,033,439 A | 3/2000 | Camino et al. |
| 6,045,582 A | 4/2000 | Prybyla |
| 6,102,953 A | 8/2000 | Huebner |
| 6,120,542 A | 9/2000 | Camino et al. |
| 6,129,764 A | 10/2000 | Servidio |
| 6,168,627 B1 | 1/2001 | Huebner |
| 6,168,628 B1 | 1/2001 | Huebner |
| 6,193,758 B1 | 2/2001 | Huebner |
| 6,197,062 B1 | 3/2001 | Fenlin |
| 6,197,063 B1 | 3/2001 | Dews |
| 6,206,925 B1 | 3/2001 | Tornier |
| 6,217,618 B1 | 4/2001 | Hileman |
| 6,228,120 B1 | 5/2001 | Leonard et al. |
| 6,283,999 B1 | 9/2001 | Rockwood, Jr. |
| 6,368,352 B1 | 4/2002 | Camino et al. |
| 6,485,520 B1 | 11/2002 | Hubach et al. |
| 6,494,913 B1 | 12/2002 | Huebner |
| 6,508,840 B1 | 1/2003 | Rockwood, Jr. et al. |
| 6,508,841 B2 | 1/2003 | Martin et al. |
| 6,520,994 B2 | 2/2003 | Nogarin |
| 6,524,342 B1 | 2/2003 | Muhlhausler et al. |
| 6,530,957 B1 | 3/2003 | Jack |
| 6,589,282 B2 | 7/2003 | Pearl |
| 6,602,292 B2 | 8/2003 | Burkinshaw |
| 6,673,114 B2 | 1/2004 | Hartdegen et al. |
| 6,679,916 B1 | 1/2004 | Frankle et al. |
| 6,719,799 B1 | 4/2004 | Kropf |
| 6,736,852 B2 | 5/2004 | Callaway et al. |
| 6,749,637 B1 | 6/2004 | Bahler |
| 6,761,740 B2 | 7/2004 | Tornier |
| 6,790,234 B1 | 9/2004 | Frankle |
| 6,800,094 B2 | 10/2004 | Burkinshaw |
| 6,818,019 B2 | 11/2004 | Horber |
| 6,887,276 B2 | 5/2005 | Gerbec et al. |
| 6,887,277 B2 | 5/2005 | Rauscher et al. |
| 6,890,358 B2 | 5/2005 | Ball et al. |
| 6,899,736 B1 | 5/2005 | Rauscher et al. |
| 6,942,699 B2 | 9/2005 | Stone et al. |
| 6,953,478 B2 | 10/2005 | Bouttens et al. |
| 6,969,406 B2 | 11/2005 | Tornier et al. |
| 6,986,790 B2 | 1/2006 | Ball et al. |
| 7,011,686 B2 | 3/2006 | Ball et al. |
| 7,033,396 B2 | 4/2006 | Tornier |
| 7,044,973 B2 | 5/2006 | Rockwood, Jr. et al. |
| 7,097,663 B1 | 8/2006 | Nicol et al. |
| 7,108,405 B2 | 9/2006 | Matts et al. |
| 7,108,719 B2 | 9/2006 | Horber |
| 7,166,132 B2 | 1/2007 | Callaway et al. |
| 7,169,184 B2 | 1/2007 | Dalla Pria et al. |
| 7,175,663 B1 | 2/2007 | Stone |
| 7,175,664 B1 | 2/2007 | Lakin |
| 7,186,269 B2 | 3/2007 | Cyprien et al. |
| 7,238,207 B2 | 7/2007 | Blatter et al. |
| 7,238,208 B2 | 7/2007 | Camino et al. |
| 7,241,314 B1 | 7/2007 | Winslow |
| 7,297,163 B2 | 11/2007 | Huebner |
| 7,303,585 B2 | 12/2007 | Horber |
| 7,309,360 B2 | 12/2007 | Tornier et al. |
| 7,329,284 B2 | 2/2008 | Maroney et al. |
| 7,338,528 B2 | 3/2008 | Stone et al. |
| 7,425,214 B1 | 9/2008 | McCarthy et al. |
| 7,445,638 B2 | 11/2008 | Beguin et al. |
| 7,462,197 B2 | 12/2008 | Tornier et al. |
| 7,465,319 B2 | 12/2008 | Tornier |
| 7,470,287 B2 | 12/2008 | Tornier et al. |
| 7,531,003 B2 | 5/2009 | Reindel |
| 7,537,618 B2 | 5/2009 | Collazo |
| 7,544,211 B2 | 6/2009 | Rochetin |
| 7,608,109 B2 | 10/2009 | Dalla Pria |
| 7,611,539 B2 | 11/2009 | Bouttens et al. |
| 7,621,961 B2 | 11/2009 | Stone |
| 7,648,530 B2 | 1/2010 | Habermeyer et al. |
| 7,678,150 B2 | 3/2010 | Tornier et al. |
| 7,753,959 B2 | 7/2010 | Berelsman et al. |
| 7,758,650 B2 | 7/2010 | Dews et al. |
| 7,785,370 B2 | 8/2010 | Collazo |
| 7,819,923 B2 | 10/2010 | Stone et al. |
| 7,854,768 B2 | 12/2010 | Wiley et al. |
| 7,918,892 B2 | 4/2011 | Huebner |
| 7,922,769 B2 | 4/2011 | Deffenbaugh et al. |
| 7,951,204 B2 | 5/2011 | Chambat et al. |
| 7,959,680 B2 | 6/2011 | Stone et al. |
| 7,981,161 B2 | 7/2011 | Choi et al. |
| 8,002,838 B2 | 8/2011 | Klotz |
| 8,002,841 B2 | 8/2011 | Hasselman |
| 8,062,376 B2 | 11/2011 | Shultz et al. |
| 8,070,820 B2 | 12/2011 | Winslow et al. |
| 8,105,385 B2 | 1/2012 | Maroney et al. |
| 8,118,875 B2 | 2/2012 | Rollet |
| 8,118,876 B2 | 2/2012 | Gupta et al. |
| 8,137,407 B2 | 3/2012 | Todd et al. |
| 8,142,510 B2 | 3/2012 | Lee et al. |
| 8,147,557 B2 | 4/2012 | Lee et al. |
| 8,157,866 B2 | 4/2012 | Winslow et al. |
| 8,182,542 B2 | 5/2012 | Ferko |
| 8,192,497 B2 | 6/2012 | Ondrla |
| 8,231,682 B2 | 7/2012 | Lafosse et al. |
| 8,236,059 B2 | 8/2012 | Stone et al. |
| 8,241,366 B2 | 8/2012 | Roche et al. |
| 8,246,687 B2 | 8/2012 | Katrana et al. |
| 8,273,130 B2 | 9/2012 | Gradl |
| 8,277,511 B2 | 10/2012 | Tornier et al. |
| 8,303,665 B2 | 11/2012 | Tornier et al. |
| 8,323,347 B2 | 12/2012 | Guederian et al. |
| 8,328,874 B2 | 12/2012 | Lee |
| 8,337,563 B2 | 12/2012 | Roche et al. |
| 8,343,226 B2 | 1/2013 | Nogarin et al. |
| 8,361,157 B2 | 1/2013 | Bouttens et al. |
| 8,419,798 B2 | 4/2013 | Ondrla et al. |
| 8,444,698 B2 | 5/2013 | Klotz et al. |
| 8,454,702 B2 | 6/2013 | Smits et al. |
| 8,460,390 B2 | 6/2013 | Biss et al. |
| 8,545,504 B2 | 10/2013 | Durand-Allen et al. |
| 8,545,511 B2 | 10/2013 | Splieth et al. |
| 8,562,686 B2 | 10/2013 | Klotz et al. |
| 8,591,591 B2 | 11/2013 | Winslow et al. |
| 8,608,805 B2 | 12/2013 | Forrer et al. |
| 8,617,249 B2 | 12/2013 | Emami |
| 8,623,092 B2 | 1/2014 | Bickley et al. |
| 8,623,093 B2 | 1/2014 | Dickerson |
| 8,632,603 B2 | 1/2014 | Hodorek et al. |
| 8,647,387 B2 | 2/2014 | Winslow |
| 8,663,334 B2 | 3/2014 | Viscardi et al. |
| 2001/0007957 A1 | 7/2001 | Martin et al. |
| 2001/0011192 A1 | 8/2001 | Ondrla et al. |
| 2001/0011193 A1 | 8/2001 | Nogarin |
| 2001/0049561 A1 | 12/2001 | Dews et al. |
| 2001/0053935 A1 | 12/2001 | Hartdegen et al. |
| 2002/0016634 A1 | 2/2002 | Maroney et al. |

(56) References Cited

U.S. PATENT DOCUMENTS

| | | |
|---|---|---|
| 2002/0099445 A1 | 7/2002 | Maroney et al. |
| 2002/0120339 A1 | 8/2002 | Callaway et al. |
| 2002/0128719 A1 | 9/2002 | Burkinshaw |
| 2003/0014119 A1 | 1/2003 | Capon et al. |
| 2003/0028253 A1 | 2/2003 | Stone et al. |
| 2003/0099519 A1 | 5/2003 | Robinson et al. |
| 2003/0114933 A1 | 6/2003 | Bouttens et al. |
| 2003/0149486 A1 | 8/2003 | Huebner |
| 2003/0158605 A1 | 8/2003 | Tornier |
| 2004/0030394 A1 | 2/2004 | Horber |
| 2004/0030396 A1 | 2/2004 | Horber |
| 2004/0039449 A1 | 2/2004 | Tornier |
| 2004/0059424 A1 | 3/2004 | Guederian et al. |
| 2004/0064187 A1 | 4/2004 | Ball et al. |
| 2004/0064188 A1 | 4/2004 | Ball et al. |
| 2004/0064190 A1 | 4/2004 | Ball et al. |
| 2004/0143336 A1 | 7/2004 | Burkinshaw |
| 2004/0143337 A1 | 7/2004 | Burkinshaw |
| 2004/0186579 A1 | 9/2004 | Callaway et al. |
| 2004/0210317 A1 | 10/2004 | Maroney et al. |
| 2004/0220673 A1 | 11/2004 | Pria |
| 2004/0220674 A1 | 11/2004 | Pria |
| 2004/0267370 A1 | 12/2004 | Ondrla |
| 2005/0033443 A1 | 2/2005 | Blatter et al. |
| 2005/0085921 A1 | 4/2005 | Gupta et al. |
| 2005/0113931 A1 | 5/2005 | Horber |
| 2005/0128755 A1 | 6/2005 | Matts et al. |
| 2005/0143829 A1 | 6/2005 | Ondrla et al. |
| 2005/0256583 A1 | 11/2005 | Bouttens et al. |
| 2005/0278030 A1 | 12/2005 | Tornier et al. |
| 2005/0278032 A1 | 12/2005 | Tornier et al. |
| 2005/0288681 A1 | 12/2005 | Klotz et al. |
| 2005/0288791 A1 | 12/2005 | Tornier et al. |
| 2006/0004462 A1 | 1/2006 | Gupta |
| 2006/0020344 A1 | 1/2006 | Shultz et al. |
| 2006/0030946 A1 | 2/2006 | Ball et al. |
| 2006/0069445 A1 | 3/2006 | Ondrla et al. |
| 2006/0079963 A1 | 4/2006 | Hansen |
| 2006/0084989 A1* | 4/2006 | Dickinson .......... A61B 17/7007 606/278 |
| 2006/0129247 A1 | 6/2006 | Brown et al. |
| 2006/0142872 A1 | 6/2006 | Klotz et al. |
| 2006/0161260 A1 | 7/2006 | Thomas et al. |
| 2006/0200247 A1 | 9/2006 | Charrois |
| 2006/0200248 A1 | 9/2006 | Beguin et al. |
| 2006/0229730 A1 | 10/2006 | Railey et al. |
| 2007/0050040 A1 | 3/2007 | Guederian et al. |
| 2007/0078519 A1 | 4/2007 | Klotz |
| 2007/0100458 A1 | 5/2007 | Dalla Pria |
| 2007/0112430 A1 | 5/2007 | Simmen et al. |
| 2007/0118230 A1 | 5/2007 | Callaway et al. |
| 2007/0156246 A1 | 7/2007 | Meswania et al. |
| 2007/0173945 A1 | 7/2007 | Wiley et al. |
| 2007/0179624 A1 | 8/2007 | Stone et al. |
| 2007/0198094 A1 | 8/2007 | Berelsman et al. |
| 2007/0225820 A1 | 9/2007 | Thomas et al. |
| 2007/0243045 A1 | 10/2007 | Gaska |
| 2007/0244563 A1 | 10/2007 | Roche et al. |
| 2007/0299527 A1 | 12/2007 | McCleary et al. |
| 2008/0221622 A1 | 9/2008 | Triplett et al. |
| 2008/0228281 A1 | 9/2008 | Forrer et al. |
| 2008/0275507 A1 | 11/2008 | Triplett et al. |
| 2008/0294268 A1 | 11/2008 | Baum et al. |
| 2008/0306600 A1 | 12/2008 | Huebner |
| 2009/0005870 A1* | 1/2009 | Hawkins .............. A61F 2/4455 623/17.11 |
| 2009/0062923 A1 | 3/2009 | Swanson |
| 2009/0099662 A1 | 4/2009 | Splieth et al. |
| 2009/0149961 A1 | 6/2009 | Dallmann |
| 2009/0164021 A1 | 6/2009 | Dallmann |
| 2009/0171462 A1 | 7/2009 | Poncet et al. |
| 2009/0192621 A1 | 7/2009 | Winslow et al. |
| 2009/0210065 A1 | 8/2009 | Nerot et al. |
| 2009/0216332 A1 | 8/2009 | Splieth et al. |
| 2009/0270993 A1 | 10/2009 | Maisonneuve et al. |
| 2009/0281630 A1 | 11/2009 | Delince et al. |
| 2009/0287309 A1 | 11/2009 | Walch et al. |
| 2010/0023068 A1 | 1/2010 | Bouttens et al. |
| 2010/0049327 A1 | 2/2010 | Isch et al. |
| 2010/0057210 A1 | 3/2010 | Ondrla |
| 2010/0087927 A1 | 4/2010 | Roche et al. |
| 2010/0125336 A1 | 5/2010 | Johnson et al. |
| 2010/0161065 A1 | 6/2010 | Williams, Jr. et al. |
| 2010/0161066 A1 | 6/2010 | Iannotti et al. |
| 2010/0211178 A1 | 8/2010 | Nogarin et al. |
| 2010/0222886 A1 | 9/2010 | Wiley et al. |
| 2010/0228352 A1 | 9/2010 | Courtney, Jr. et al. |
| 2010/0234959 A1 | 9/2010 | Roche et al. |
| 2011/0054624 A1 | 3/2011 | Iannotti |
| 2011/0060417 A1 | 3/2011 | Simmen et al. |
| 2011/0082557 A1 | 4/2011 | Mutchler et al. |
| 2011/0098822 A1 | 4/2011 | Walch et al. |
| 2011/0106267 A1 | 5/2011 | Grant |
| 2011/0118846 A1 | 5/2011 | Katrana |
| 2011/0153023 A1 | 6/2011 | Deffenbaugh et al. |
| 2011/0178604 A1 | 7/2011 | Porter |
| 2011/0196491 A1 | 8/2011 | Huebner |
| 2011/0295376 A1 | 12/2011 | Winslow |
| 2012/0029647 A1 | 2/2012 | Winslow et al. |
| 2012/0179262 A1 | 7/2012 | Metcalfe et al. |
| 2012/0191201 A1 | 7/2012 | Smits et al. |
| 2012/0209392 A1 | 8/2012 | Angibaud et al. |
| 2012/0221112 A1 | 8/2012 | Lappin |
| 2012/0253467 A1 | 10/2012 | Frankle |
| 2012/0259334 A1 | 10/2012 | Splieth et al. |
| 2012/0265315 A1 | 10/2012 | Kusogullari et al. |
| 2012/0271425 A1 | 10/2012 | Maurer |
| 2012/0271426 A1 | 10/2012 | Roche et al. |
| 2012/0277880 A1 | 11/2012 | Winslow et al. |
| 2012/0303130 A1 | 11/2012 | Winslow et al. |
| 2013/0006369 A1 | 1/2013 | Wiley et al. |
| 2013/0060341 A1 | 3/2013 | Tornier et al. |
| 2013/0090736 A1 | 4/2013 | Katrana et al. |
| 2013/0197650 A1 | 8/2013 | Smits et al. |
| 2013/0197651 A1 | 8/2013 | McDaniel et al. |
| 2013/0197652 A1 | 8/2013 | Ekelund et al. |
| 2013/0204375 A1 | 8/2013 | Winslow et al. |
| 2013/0245775 A1 | 9/2013 | Metcalfe |
| 2013/0261750 A1 | 10/2013 | Lappin |
| 2013/0267960 A1 | 10/2013 | Groh |
| 2013/0282129 A1 | 10/2013 | Phipps |
| 2013/0325130 A1 | 12/2013 | Viscardi et al. |
| 2013/0325131 A1 | 12/2013 | Roche et al. |
| 2013/0325133 A1 | 12/2013 | Viscardi et al. |
| 2013/0325134 A1 | 12/2013 | Viscardi et al. |
| 2014/0018927 A1 | 1/2014 | De Wilde et al. |
| 2014/0039633 A1 | 2/2014 | Roche et al. |
| 2014/0039634 A1 | 2/2014 | Klotz |
| 2014/0350615 A1 | 11/2014 | Holovacs et al. |

FOREIGN PATENT DOCUMENTS

| | | |
|---|---|---|
| EP | 1314407 A1 | 5/2003 |
| EP | 1520560 | 4/2005 |
| EP | 1656910 A1 | 5/2006 |
| EP | 2047827 A1 | 4/2009 |
| EP | 2201912 A1 | 6/2010 |
| FR | 2689756 | 10/1993 |
| FR | 2699400 | 6/1994 |
| GB | 2001247 A | 1/1979 |
| GB | 2405346 A | 3/2005 |
| WO | 0147442 A1 | 7/2001 |
| WO | 2005032430 | 4/2005 |
| WO | 2007031575 A1 | 3/2007 |
| WO | 2007039820 | 4/2007 |
| WO | 2007084939 | 7/2007 |
| WO | 2008000928 A2 | 1/2008 |

OTHER PUBLICATIONS

Delta Reverse Shoulder System, Surgical Technique, DePuy 2004.
European Search Report, EP 10156704, dated Jun. 14, 2010.

(56) References Cited

OTHER PUBLICATIONS

Extended European Search Report for Application No. 12183703 dated Jan. 30, 2013.
Extended European Search Report for Application No. EP12195588 dated Mar. 1, 2013.
Extended European Search Report for Application No. EP13169019 dated Jul. 26, 2013.
Extended European Search Report, EP 08166202, dated Feb. 5, 2009.
Mode Operatoire, Operative Technique, Arrow, date not known.
Reverse Shoulder Prosthesis, Surgical Technique, Encore, 2005.
Trabecular Metal Reverse Shoulder System, Zimmer, date not known.
Zimmer, Anatomical Shoulder Fracture System / Surgical Technique, 24 pages, Revised Jan. 4, 2010.

\* cited by examiner

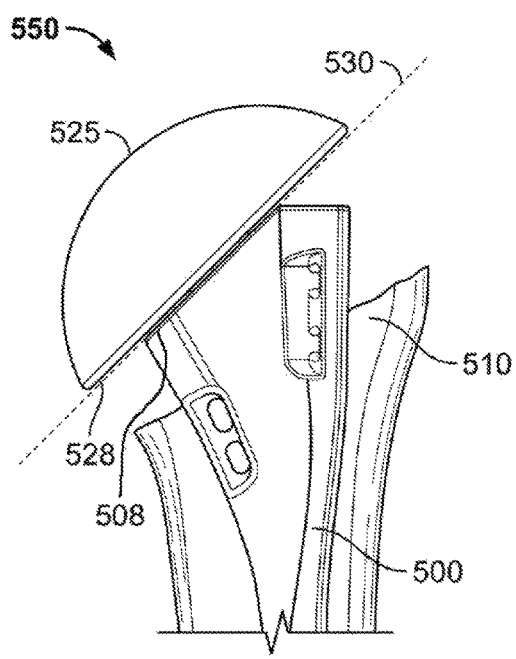
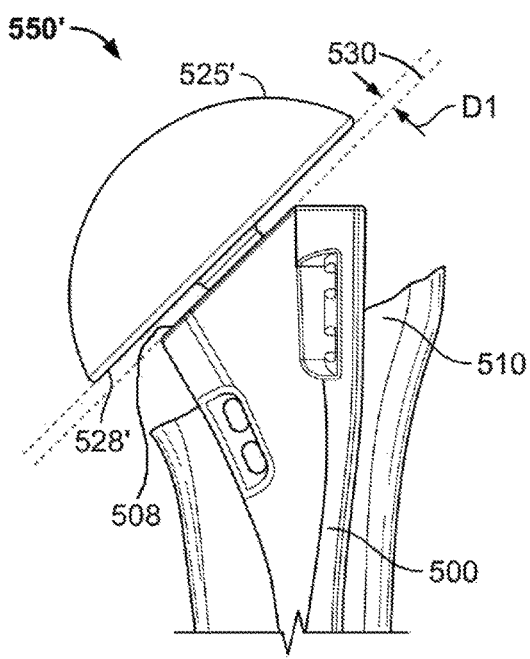
FIG. 8A
FIG. 8B

HUMERAL TRIAL ADAPTOR

FIELD OF THE INVENTION

The present invention relates to an orthopedic trial adaptor for use with both standard and reverse shoulder arthroplasty systems in a cemented, fracture or any similar setting where the final seating height of the head or cup implant is not readily available. The thickness of the orthopedic trial adaptor takes into account the difference in coupling between a trial which sits flush on a humeral stem and an implant which sits proudly on the humeral stem.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, for example, which normally provides a cushioning effect, to wear down. When the cartilage wears down, fluid can accumulate in the joint areas, resulting in pain, stiffness, and decreased mobility. The same can happen in the case where tendons in a joint become lax or soft tissues in or adjacent the joint tear becomes damaged or worn.

Arthroplasty procedures can be used to repair damaged joints. During a typical arthroplasty procedure, an arthritic or otherwise dysfunctional joint can be remodeled or realigned, or an implant or implants can be implanted into the damaged region. Arthroplasty procedures may take place in any of a number of different regions of the body, such as a knee, a hip, a shoulder, or an elbow.

One type of arthroplasty procedure is a shoulder arthroplasty, in which a damaged shoulder joint is replaced with prosthetic implants. The shoulder joint may have been damaged by, for example, arthritis (e.g., severe osteoarthritis or degenerative arthritis), trauma, or a rare destructive joint disease.

Implants that are implanted into a damaged region may provide support and structure to the damaged region, and may help to restore the damaged region, thereby enhancing its functionality. Prior to implantation of an implant in a damaged region, the damaged region may be prepared to receive the implant. In the case of a shoulder arthroplasty procedure, one or more of the bones in the shoulder area, such as the humerus and/or glenoid, may be treated (e.g., cut, drilled, reamed, and/or resurfaced) to provide one or more surfaces that can align with the implant and thereby accommodate the implant. Standard alignment instrumentation may be used for locating a position and orientation to resect the humeral head for proper humeral stem placement in the humerus.

Accuracy in implant alignment is an important factor to the success of the procedure. A one to two millimeter translational misalignment, or a few degrees of rotational misalignment, may result in imbalanced ligaments, and may thereby significantly affect the outcome of the procedure. For example, implant misalignment may result in intolerable post-surgery pain, and also may prevent the patient from having proper deltoid tension or range of motion.

To achieve accurate implant alignment, prior to treating (e.g., cutting, drilling, reaming, and/or resurfacing) any regions of a bone, it is important to correctly determine the location at which the treatment will take place and how the treatment will be oriented. Accordingly, instruments such as trials have been developed to be used in this part of the procedure. Generally, trials are affixed to the bone during joint kinematic evaluation and removed therefrom after a proper position and orientation for the implant has been determined.

Typically, trials are designed to correspond to an implant in size and shape. In a shoulder arthroplasty procedure, for example, a trial stem may be designed to be temporarily inserted into a prepared medullary canal of the humerus in a manner similar to that of an implant. Known trials may take many forms. For example, an expanding trial stem, such as that described in U.S. Pat. No. 8,216,320, the entire contents of which are hereby incorporated by reference herein, includes a trial stem that may be expanded after insertion into the medullary canal. When using such trial stems, particularly in shoulder replacements, it may be difficult to establish the proper position and orientation for the implant in the humerus. Further, trial cups and heads may be coupled to the trial stem during the trialing procedure. In order to achieve proper deltoid tension in a shoulder arthroplasty procedure, any differences in positioning between the trials and the corresponding implants should be taken into account.

BRIEF SUMMARY OF THE INVENTION

Humeral trial cups and heads of the present invention have connector or shaft portions for coupling the trial cups and heads to a corresponding humeral stem. While the trials are configured to sit flush with the stem, the implant head or cup sits proudly on the stem to ensure their tapered connection features are always properly engaged. A trial adaptor of the present invention is used to take into account the planar distance by which the implant head or cup sits proudly on the stem. The planar distance is defined by the distance between a base surface of the implant head or cup and a neck or contact surface of the stem.

A first aspect of the present invention is an orthopedic trialing system comprising a stem, an adaptor and a cup. The stem has a first coupling feature and a shaft portion adapted to be received in a canal of a bone of a patient. The adaptor has top and bottom surfaces and an aperture through the top and bottom surfaces. The cup has a second coupling feature, wherein one of the first and second coupling features extends through the aperture of the adaptor and at least partially into the other of the first and second coupling features for coupling together the cup, the adaptor and the stem.

In one embodiment of the first aspect, the bottom surface of the adaptor contacts and lies adjacent to a contact surface of the stem when the cup, the adaptor and the stem are coupled together. In another embodiment, when the top surface of the adaptor contacts and lies adjacent to a contact surface of the cup, the adaptor and the stem are coupled together.

According to the first aspect of the present invention, each of the top and bottom surfaces of the adaptor and the contact surfaces of the cup and stem are planar. In one embodiment, the first coupling feature of the stem is a recess, the stem having a contact surface with the recess therein. The second coupling feature of the cup is a protrusion that extends through the aperture of the adaptor and at least partially into the recess of the stem when the cup, the adaptor and the stem are coupled together.

In another embodiment, the first coupling feature is a protrusion, the stem having a contact surface with the protrusion extending outwardly therefrom. The second coupling feature of the cup is a recess and the protrusion of the stem extends through the aperture of the adaptor and at least partially into the recess of the cup when the cup, the adaptor and the stem are coupled together.

In yet another embodiment, the adaptor includes an engagement feature adapted to couple the adaptor to the stem.

In still yet another embodiment, the stem is selected from the group consisting of a broach, a trial stem or a prosthesis stem.

A second aspect of the present invention is an orthopedic trialing system comprising a stem, an adaptor and a cup. The stem has a planar surface and a shaft portion adapted to be received in a canal of a bone of a patient. The adaptor has a thickness defined by a linear distance between top and bottom surfaces thereof. The cup has a planar surface, wherein the planar surface of the stem and the planar surface of the cup are separated by the thickness of the adaptor when the cup, the adaptor and the stem are coupled together.

A third aspect of the present invention is an orthopedic trialing system comprising a stem, an adaptor and a cup. The stem having a shaft portion adapted to be received in a canal of a bone of a patient. The adaptor having top and bottom surfaces and an aperture through the top and bottom surfaces. The cup having a coupling feature for coupling together the cup, the adaptor and the stem.

In each of the above described aspects of the invention, the orthopedic trial system comprises a stem, an adaptor and a cup. However, in other aspects of the present invention, the cup that is used in reverse shoulder cases can be replaced with a head that is used in a total arthroplasty procedure. In other words, the orthopedic trial system in total arthroplasty cases includes a stem, an adaptor and a head.

BRIEF DESCRIPTION OF THE DRAWINGS

FIG. 8A is a front view of one embodiment of a humeral head trial coupled to a stem implant of FIG. 5A inserted into a fractured humeral bone.

FIG. 8B is a front view of one embodiment of a humeral head implant coupled to a stem implant of FIG. 5A inserted into a fractured humeral bone.

DETAILED DESCRIPTION

In describing preferred embodiments of the disclosure, reference will be made to the directional nomenclature used in describing the human body. It is noted that this nomenclature is used only for convenience and that it is not intended to be limiting with respect to the scope of the invention. When referring to specific directions in relation to a device, the device is understood to be described only with respect to its orientation and position during an exemplary application to the human body. As used herein when referring to bones or other parts of the body, the term "proximal" means closer to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body. Further, although the devices and methods described herein are generally described in relation to human shoulder replacements, it should be understood that the devices and methods are not intended to be so limited and could be used with other joints, such as other ball and socket joints, including the hip, for example.

Figure 1A:
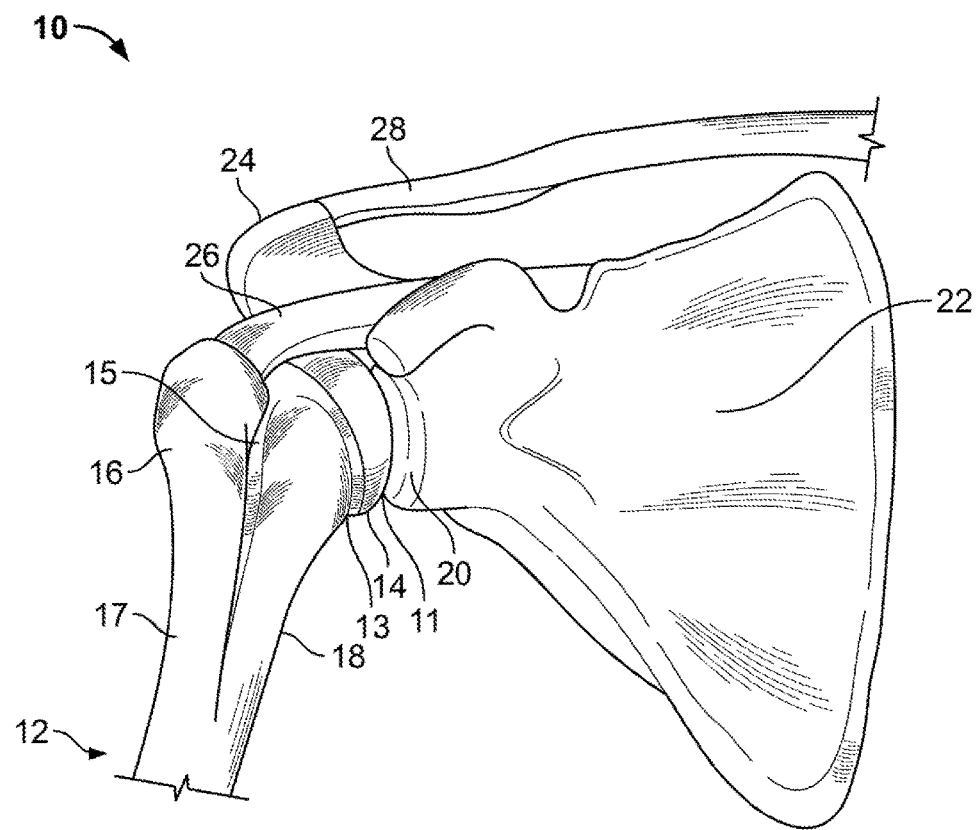
FIG. 1A shows the general shoulder joint anatomy of a patient.
Figure 1B:
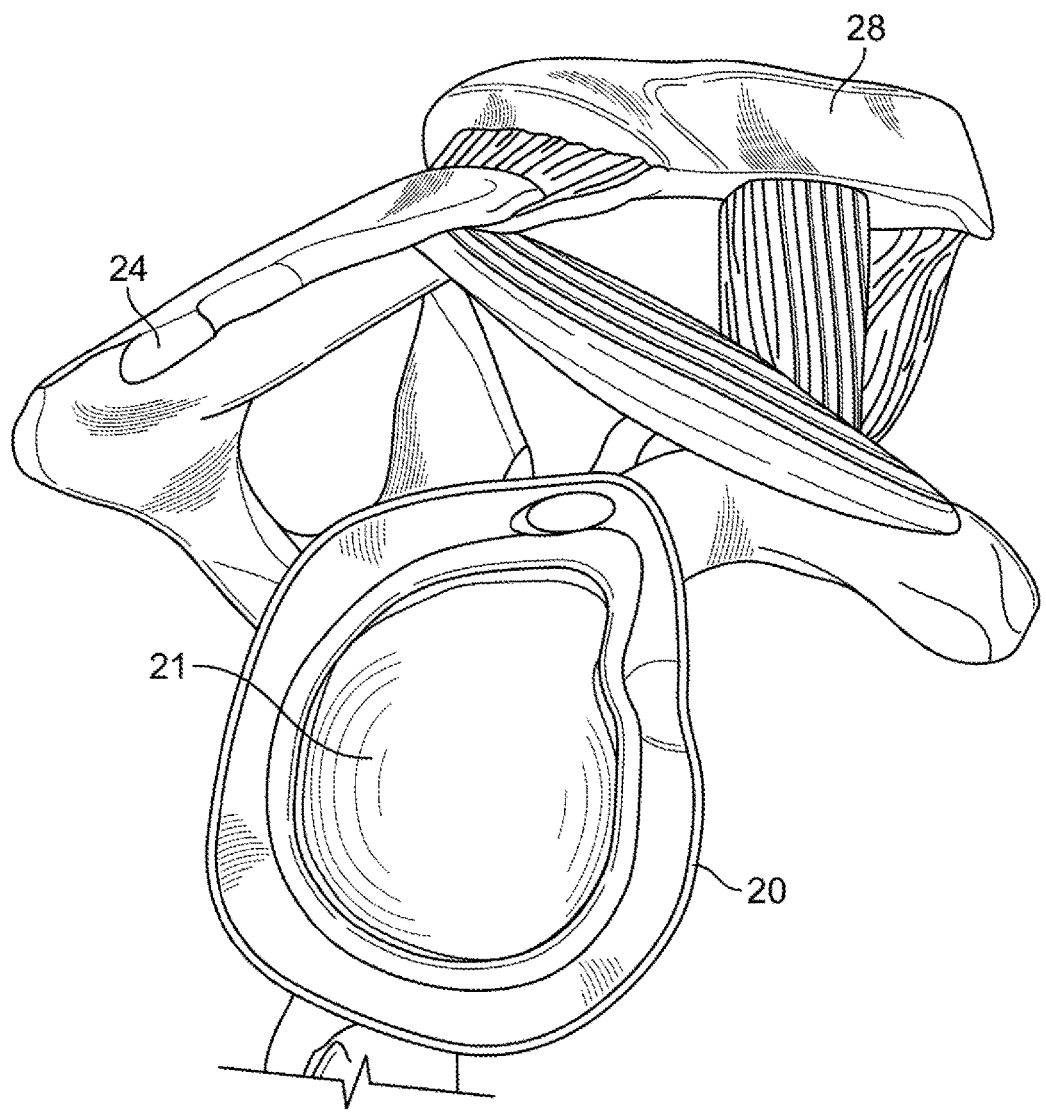
FIG. 1B is a view of a glenoid cavity of the shoulder joint.

FIGS. 1A-B show the general anatomy of shoulder joint 10 of a patient. As shown in FIG. 1A, humerus 12 of joint 10 includes a neck portion 13, a head portion 14 and a shaft portion 17 having a greater tuberosity 16 and a lesser tuberosity 18. Between greater and lesser tuberosities 16, 18 is bicipital groove 15. As shown in FIG. 1B, scapula 22 terminates at glenoid 20 having a cavity 21 in which an outer surface 11 of head portion 14 rotates within. Along with humerus 12 and scapula 22, the acromion 24, rotator cuff 26 and clavicle 28 all provide support to the range of motion of the shoulder joint 10 of the patient.

Figure 2:
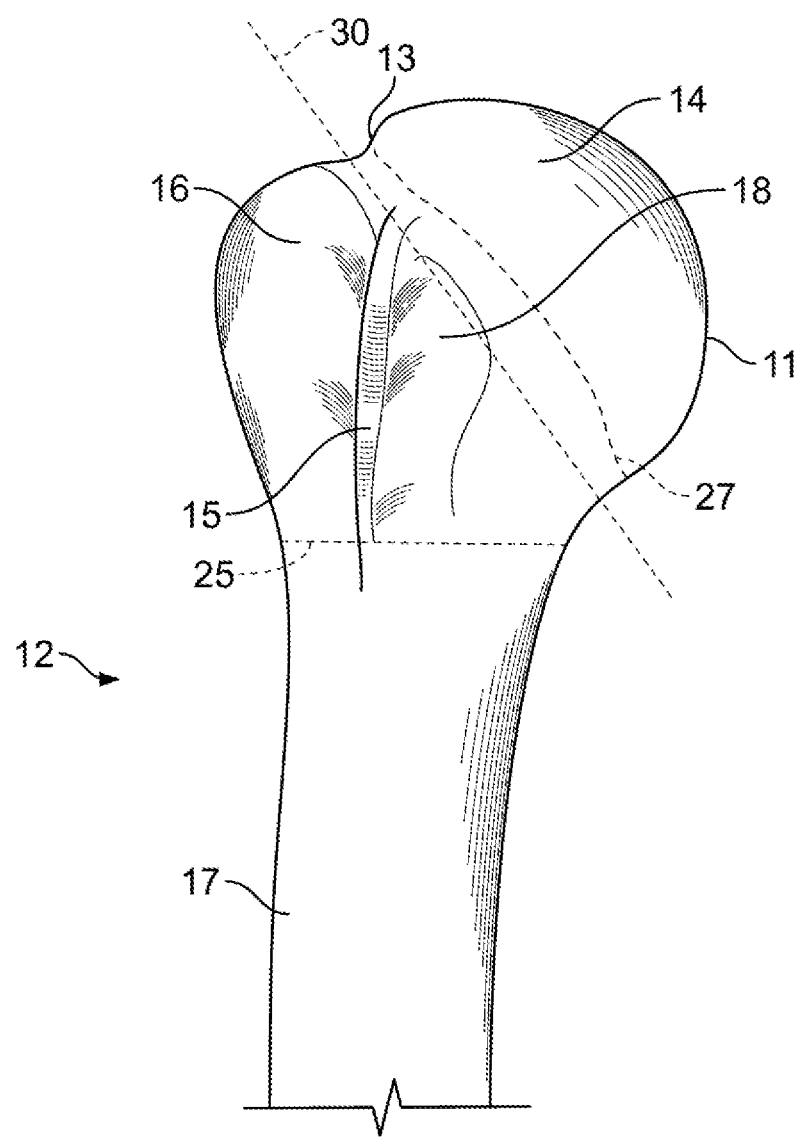
FIG. 2 is a posterior view of a proximal portion of a humerus of the shoulder joint showing a resection line adjacent the anatomical neck of a humerus.

FIG. 2 is a posterior view of a proximal portion of humerus 12 of shoulder joint 10. Head portion 14 includes outer surface 11. Also shown is bicipital groove 15, a substantially straight surgical neck line 25 and a curvy anatomical neck line 27. Outer surface 11, biciptal groove 15, substantially straight surgical neck line 25 and curvy anatomical neck line 27 are all anatomical features of humerus 12 that can be used to aid in determining the proper neck resection line.

Prior to a total shoulder arthroplasty procedure being conducted, shoulder joint 10 is generally compromised through injury or general wear and tear. A compromised joint generally leads to range of motion difficulty and pain for the patient. In a joint 10 that is compromised, head portion 14 and/or glenoid cavity 21 may be degenerated such that the axis of rotation of the shoulder joint is not in the same location as it was prior to joint 10 being compromised.

The axis of rotation of the shoulder joint varies based upon the type of motion. For flexion and extension, the axis of rotation is a transverse axis though the center of the humeral head. For abduction and adduction, the axis of rotation is a sagittal axis thought the center of the humeral head. For internal and external rotation, the axis of rotation is a vertical axis though the center of the humeral head.

During a total shoulder arthroplasty procedure, the humerus is resected in order to receive a humeral stem component. In such a procedure, the humeral head is generally resected and the shaft of the humerus is reamed to receive the humeral stem component prosthesis. It is important that the humeral stem component be positioned in the correct location and orientation in order to restore the axis of rotation of joint 10. Some humeral stem components may include a flange that is adapted to contact a flat portion of resected bone of the humerus in order to correctly position and stabilize the humeral stem component within shaft 17 of humerus 12 such that the axis of rotation of joint 10 may be restored.

Also during a total shoulder arthroplasty procedure, the glenoid is resected in order to receive a glenoid component. In a shoulder arthroplasty procedure for implanting a reverse shoulder prosthesis, a cavity of the glenoid may be reamed and a guide hole may be drilled in order to receive a central screw extending outwardly from an outer contact surface of the glenoid component. The location and orientation of the guide hole may be based on the shape of the glenoid component, for example, such that the glenoid component can be implanted in the resected glenoid cavity and the axis of rotation of the joint may be restored. It is important that the glenoid component be positioned in the correct location and orientation in order to restore the axis of rotation of joint 10. The glenoid component preferably has an articular surface corresponding to an outer surface of a humeral head component which is engaged to the humeral stem component implanted at least partially within the shaft of the humerus. Generally, the glenoid component has a diameter that is approximately 6 mm in diameter larger than the humeral head component.

As discussed above, humerus 12 must be resected at the correct location and orientation in order for a corresponding humeral stem prosthesis to be accurately implanted in shaft 17 of humerus 12 such that the axis of rotation of the shoulder joint may be restored. Thus, the location and orientation of resection line 30, as shown in FIG. 2, is either preoperatively or intraoperatively planned according to a desired result of the arthroplasty procedure.

Figure 3:
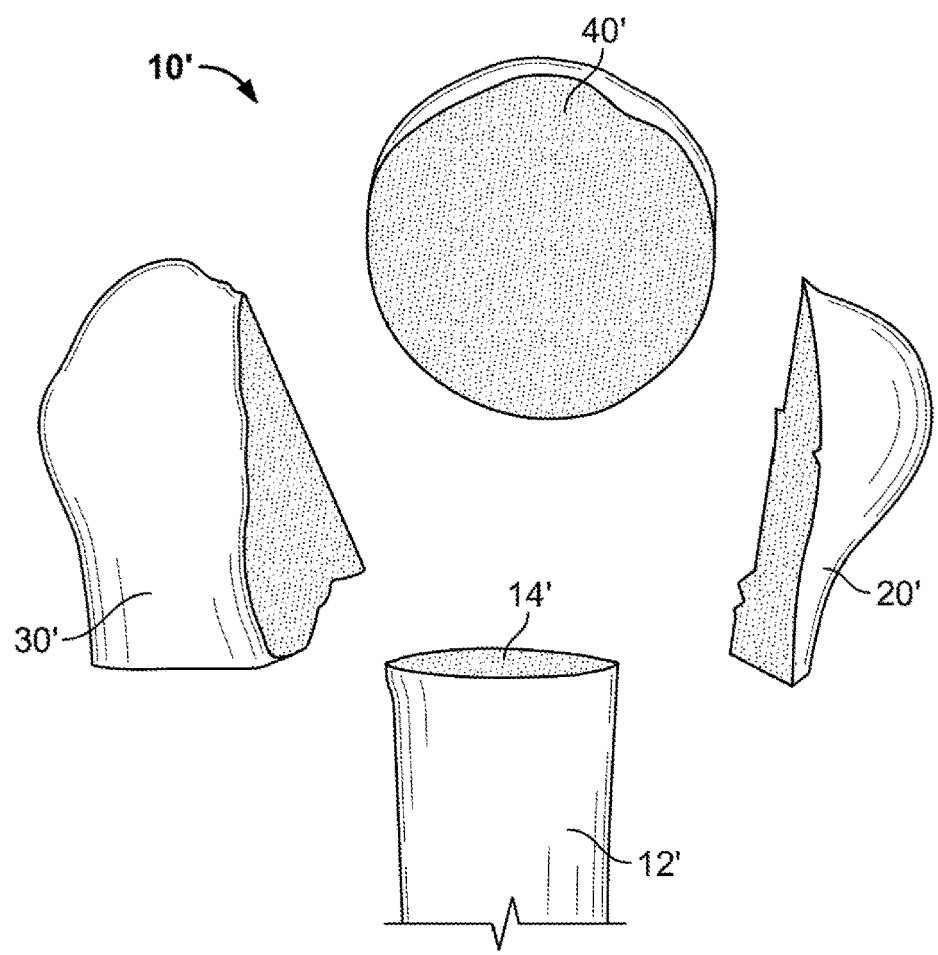
FIG. 3 is a schematic view of an exemplary proximal humerus broken into a plurality of bone fragments.

Generally, the replacement of a humeral head with a prosthetic implant during shoulder arthroplasty involves gaining access to the shoulder joint through a retracted incision and removing the damaged humeral head. An exemplary damaged proximal humerus 10' is illustrated in FIG. 3. Although such breaks giving rise to a plurality of bone fragments may occur in any number of ways, this particular humerus 10' is broken such that a first segment 20', a second segment 30', and a third segment 40' including a substantial portion of the humeral head are each detached from the proximal end 12' of the humerus. After removal of the humeral head, the proximal end of the humeral medullary canal may be shaped in order to accept an implant according to known methods. In one exemplary method, a hand reamer, for example, may be used at a proximal humeral bearing surface 14' to remove bone material until an appropriately-shaped opening is formed in the proximal end 12' of humerus 10' for receiving an implant. Typically, successive reamers of increasing size are used in order to form an opening of the desired size. In many cases, bearing surface 14' may not be as flat as shown. Most surfaces at a fracture site are irregularly shaped unless there is a clean break between adjacent fragments. Such a surface may be resected into a generally flat shape to receive a corresponding bearing surface of a trial and/or implant stem as shown in FIG. 3.

Figure 4:
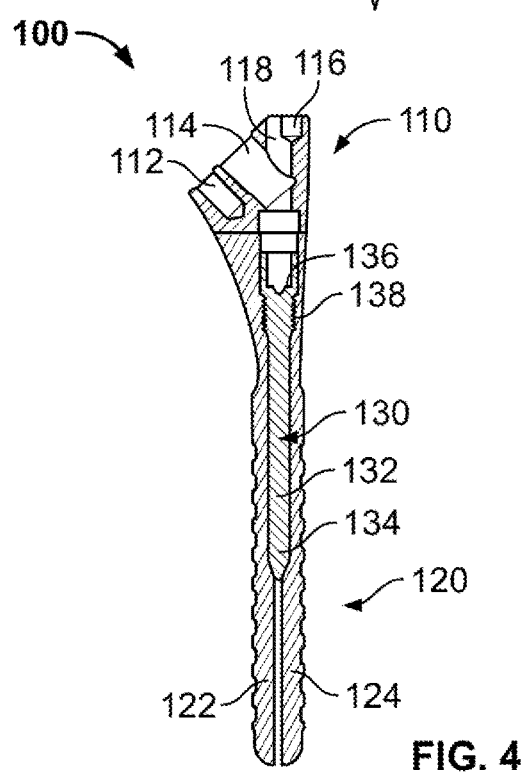
FIG. 4 is a cross-sectional view of one embodiment of a trial stem for use during a shoulder replacement procedure.
Figure 7A:
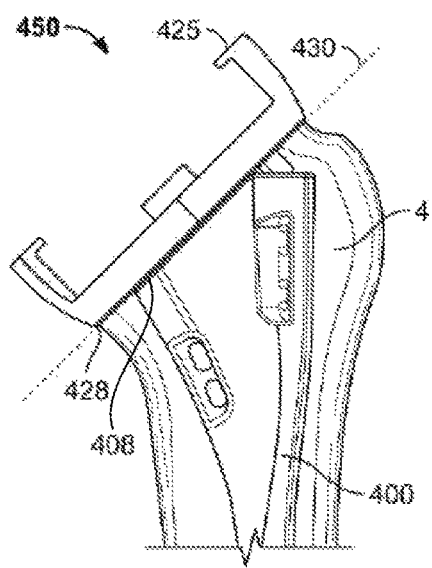
FIG. 7A is a front view of one embodiment of a humeral cup trial coupled to a stem implant of FIG. 5A inserted into a resected humeral bone.
Figure 11A:
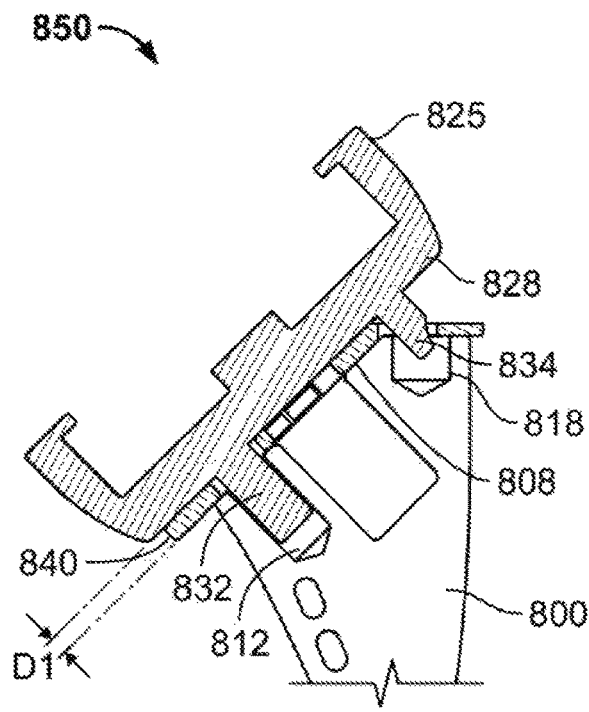
FIG. 11A is a front cross-sectional view of one embodiment of a humeral cup trial, humeral trial adaptor and stem implant coupled to one another.
Figure 11B:
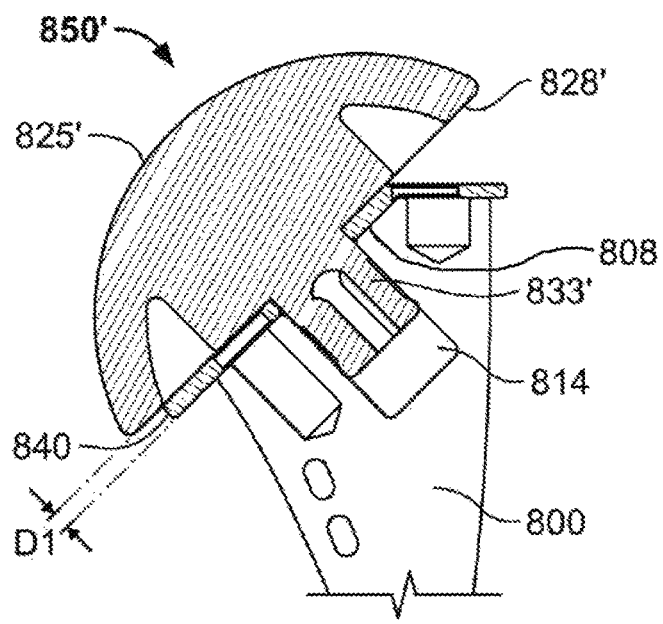
FIG. 11B is a front cross-sectional view of one embodiment of a humeral head trial, humeral trial adaptor and stem implant coupled to one another.

Once an appropriate bearing surface 14 and opening is formed for receiving an implant, trialing is conducted to determine the proper size and location for the implant prior to implantation thereof. According to one example of the present disclosure, trialing includes inserting a trial stem 100, as illustrated in FIG. 4, into the opening in the proximal end 12 of humerus 10. Trial stem 100 may include a proximal portion 110 connected to a distal portion 120, for example by welding, with an expansion bolt 130 positioned within the trial stem. Generally, proximal portion 110 is adapted for insertion into the proximal end 12 of a prepared humerus 10. Proximal portion 110 may include a first catch aperture 112, a trial recess 114, two second catch apertures 116 (both not visible in FIG. 4) and a driver recess 118. Catch aperture 112 and driver recess 118 may be configured to mate with a trial cup, for example, as shown in FIG. 7A or as shown in greater detail with respect to the reverse cup humeral trial show in FIG. 11A and described in U.S. Pat. No. 8,545,511, the entire contents of which are hereby incorporated by reference herein. Trial recess 114 may be shaped to receive a corresponding portion of a trial humeral head, for example, as shown in FIG. 11B. Trial recess 114 may have a longitudinal axis that is angled with respect to a longitudinal axis of distal portion 120 so as to substantially replicate the typical geometry of a shaft and neck of the native bone prior to a fracture situation as shown in FIG. 3.

The distal portion 120 of trial stem 100 may be structured to fit within a prepared bone canal, preferably the medullary canal of the humerus 10. Distal portion 120 projects along a longitudinal axis thereof from proximal portion 110 generally in the proximal-to-distal direction. Distal portion 120 may include a first arm 122 and a second arm 124 configured to move away from each other in cooperation with expansion bolt 130, such as that described in U.S. Pat. No. 8,216,320, the entire contents of which are hereby incorporated by reference herein. Distal portion 120, or a portion thereof, may define a cavity or configured to accept expansion bolt 130, the cavity including a mating surface such as threads.

Expansion bolt 130 may generally include a shaft 132 with a pointed distal tip 134. A proximal end of expansion bolt 130 may include a head 136, which may include a recess, such as a hex recess, to cooperate with a correspondingly shaped driving tool (not shown). A proximal end of shaft 132 may include a mating surface, such as threads 138, configured to mate with a corresponding surface in the cavity of distal portion 120. Although proximal portion 110, distal portion 120, and expansion bolt 130 may each be separate pieces prior to assembly, trial stem 100 is preferably provided to the end user as a single piece with the proximal and distal portions permanently connected, for example by welding, with the expansion bolt contained therein.

Figure 5A:
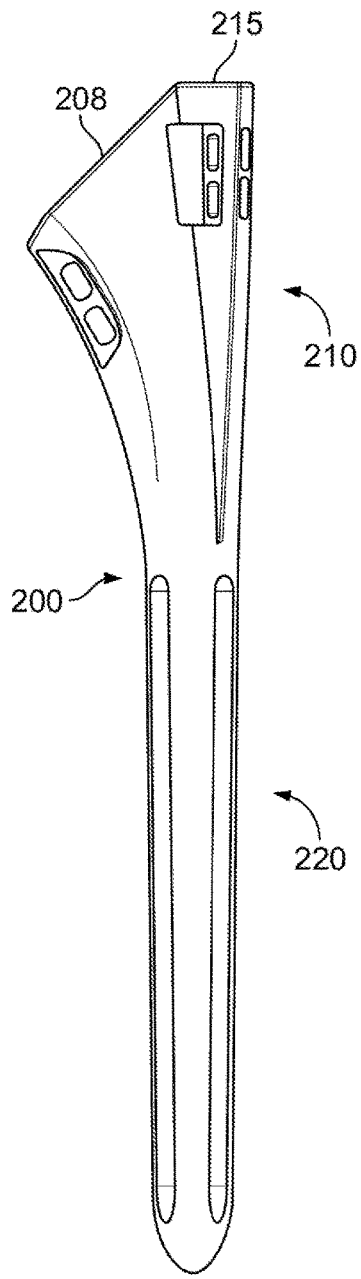
FIG. 5A is a perspective view of one embodiment of a stem implant according to aspects of the disclosure.
Figure 5B:
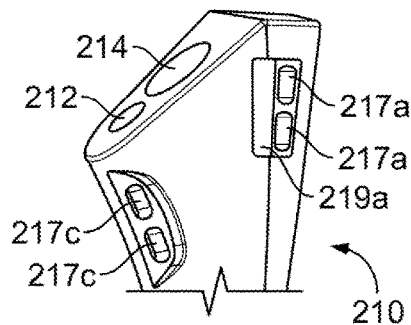
FIG. 5B is a perspective view of a proximal portion of the stem implant of FIG. 5A.
Figure 5C:
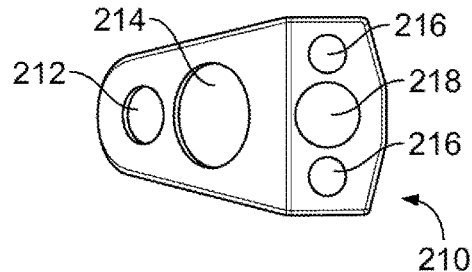
FIG. 5C is a top view of the stem implant of FIG. 5A.
Figure 5D:
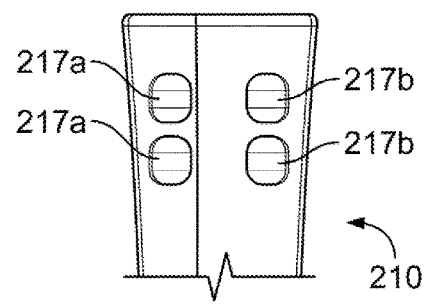
FIG. 5D is a side view of a proximal portion of the stem implant of FIG. 5A.

An exemplary embodiment of stem implant 200 is illustrated in FIG. 5A and may be structurally similar to trial stem 100 in certain respects. Stem implant 200 may be monolithic with a proximal portion 210 and a distal portion 220. Proximal portion 210 of stem implant 200, shown in greater detail in FIGS. 5B-D, may include a first contact surface 208 having a first catch aperture 212 and an implant recess 214 and a second contact surface 215 having two locking pin apertures 216 and a second catch aperture 218. The apertures 212 and 218 similar to corresponding features on trial stem 100, facilitate the connection between features of a trial cup with stem implant 300. Implant recess 214 may be configured to accept a humeral head trial or implant, reverse cup humeral implant, or other compatible implant. Proximal portion 210 may also include a number of features to facilitate securing portions of humerus 10, such as first segment 20' and second segment 30', to stem implant 200. For example, a first pair of suture holes 217a may be formed on a lateral-anterior side of proximal portion 210 and a second pair of suture holes 217b may be formed on a lateral-posterior side of the proximal portion. A third pair of suture holes 217c may be formed on a medial side of proximal portion 210. The suture holes 217a-c may facilitate securing one or more bone fragments to stem implant 200 via sutures (not illustrated). One suture pocket 219a may be formed on the lateral-anterior side of proximal portion 210, and may be connected to suture holes 217a. Another suture pocket (not visible in FIGS. 5A-D) may be formed on the lateral-posterior side of proximal portion 210, and may be connected to suture holes 217b. The suture pockets may, for example, facilitate the insertion of a suture needle.

Figure 6A:
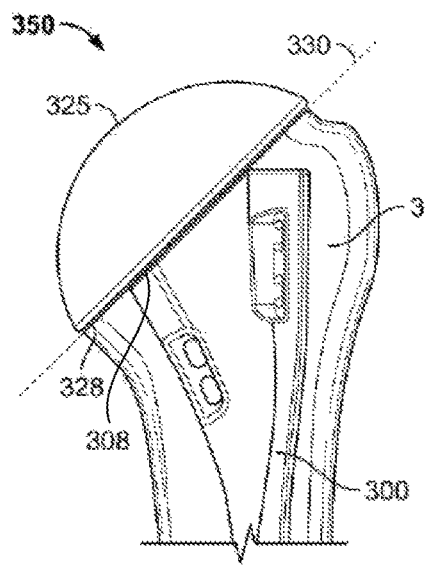
FIG. 6A is a front view of one embodiment of a humeral head trial coupled to a stem implant of FIG. 5A inserted into a resected humeral bone.
Figure 6B:
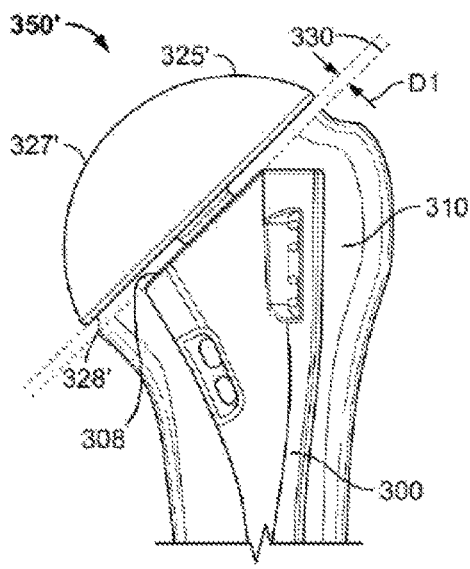
FIG. 6B is a front view of one embodiment of a humeral head implant coupled to a stem implant of FIG. 5A inserted into a resected humeral bone.

FIGS. 6A-B are exemplary embodiments of trial head and implant head assemblies 350, 350'. In FIG. 6A, a trial head 325 is coupled to a stem implant 300 inserted into a resected humeral bone 310, while in FIG. 6B, an implant head 325' is coupled to stem implant 300. A base surface 328, 328' of the respective trial head 325 and implant head 325' lie on resection or neck line 330 of resected humerus 310. As shown in FIG. 6A, base surface 328 of trial head 325 sits flush against a corresponding first contact surface 308 when trial head 325 is securely coupled to stem implant 300. In contrast, as shown in FIG. 6B, when implant head 325' is securely coupled to stem implant 300, base surface 328' of implant head 325' is separated from first contact surface 308 such that implant head 325' sits proudly on stem implant 300. The gap between base surface 328' and first contact surface 308 ensures that the tapers between the engagement portions of the implant head 325' and stem implant 300 always engage. The gap between generally parallel base surface 328' and first contact surface 308 may be defined as a linear distance D1. D1 is generally 1-2 mm in length. The range of D1 generally occurs due to the tolerances on the tapers of the implant head 325' and the stem implant 300. In a total or reverse shoulder case where you have a defined resection line 330, this gap does not affect the final position of implant head 325' because stem implant 300 will generally subside such that base surface 328' of implant head 325' lies adjacent resection line 330 and articulating surface 327' of implant head 325' will match the position of an articulating surface 327 of trial head 325 that was located during trialing. Implant head 325' may also be impacted until base surface 328' comes in contact with both resection line 330 and first contact surface 308 of stem implant 300.

Figure 7B:
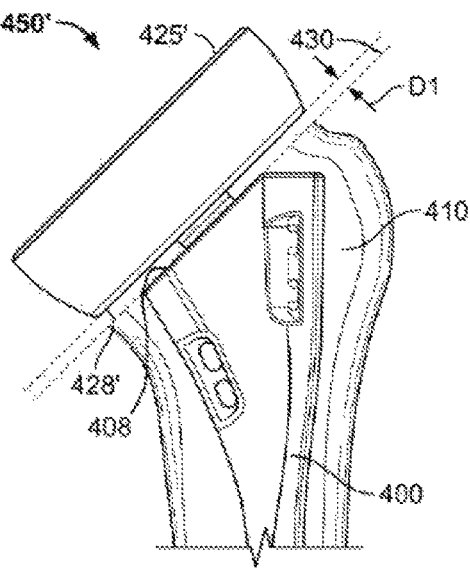
FIG. 7B is a front view of one embodiment of a humeral cup implant coupled to a stem implant of FIG. 5A inserted into a resected humeral bone.

FIGS. 7A-B are exemplary embodiments of humeral cup trial and head assemblies 450, 450'. In FIG. 7A, a trial cup 425 is coupled to a stem implant 400 inserted into a resected humeral bone 410, while in FIG. 7B, an implant cup 425' is coupled to stem implant 400. A base surface 428, 428' of the respective trial cup 425 and implant cup 425' lie on resection or neck line 430 of resected humerus 410. As shown in FIG. 7A, base surface 428 of trial cup 425 sits flush against a corresponding first contact surface 408 when trial cup 425 is securely coupled to stem implant 400. In contrast, as shown in FIG. 7B, when implant cup 425' is securely coupled to stem implant 400, base surface 428' of implant cup 425' is separated from first contact surface 408 such that implant cup 425' sits proudly on stem implant 400. The gap between base surface 428' and first contact surface 408 ensures that the tapers between the engagement portions of the implant cup 425' and stem implant 400 always engage. The gap between generally parallel base surface 428' and first contact surface 408 may be defined by linear distance D1 as shown in corresponding FIG. 6B. D1 therefore does not affect the final position of implant cup 425' because stem implant 400 will generally subside such that base surface 428' of implant cup 425' lies adjacent resection line 430 and articulating surface 427' of implant cup 425' will match the position of an articulating surface 427 of trial cup 425 that was located during trialing.

FIGS. 8A-B are exemplary embodiments of trial head and implant head assemblies 450, 450'. However, in FIGS. 8A-8B, as opposed to FIGS. 6A-6B, the stem implants are inserted into fractured humeral bone rather than resected humeral bone. In most fracture situations a defined resection line cannot be produced. Therefore, separate instrumentation such as that described in U.S. Pat. Pub. No. 2015/0328015 titled "Guides for Fracture System" which is incorporated by reference herein in its entirety and/or skill of a surgeon is generally used to determine proper stem placement to achieve a desired location and orientation of an implant head. In FIG. 8A, a trial head 525 is coupled to a stem implant 500 inserted into a fractured humeral bone 510, while in FIG. 8B, an implant head 525' is coupled to stem implant 500. A base surface 528 of trial head 525 lies on an anatomical neck line 530 as shown in FIG. 8A. In contrast, as shown in FIG. 8B, anatomical neck line 530 lies on first contact surface 508 and is separated from a base surface 528' by linear distance D1. With a fracture setting, there is no resection plane to act as a reference for the seating of trial head 525 or implant head 525'. Further, subsiding of stem implant 500 is generally not possible due to lack of reference plane and the fact that the stem is typically cemented into the fractured humerus prior to impaction of head implant. Because of the gap between implant head 525' and stem implant 500, the implant head 525' will generally sit approximately 1.5 mm higher than the trial head 525. In other words, base surface 528' or implant head 525' sits approximately 1.5 mm from the anatomical neck line 530 when implant head 525' is coupled to stem implant 500. Such a situation would also occur in non-fracture settings where a reference resection plane is not available to determine the final head implant seating height or the stem is cemented prior to impaction of the head implant.

Figure 9A:
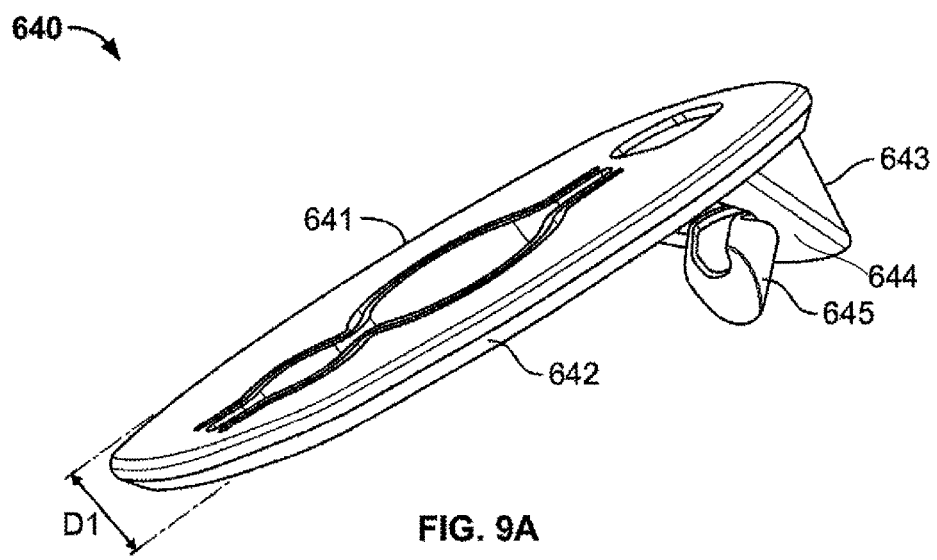
FIG. 9A is a perspective view of one embodiment of a humeral trial adaptor of the present invention.
Figure 9B:
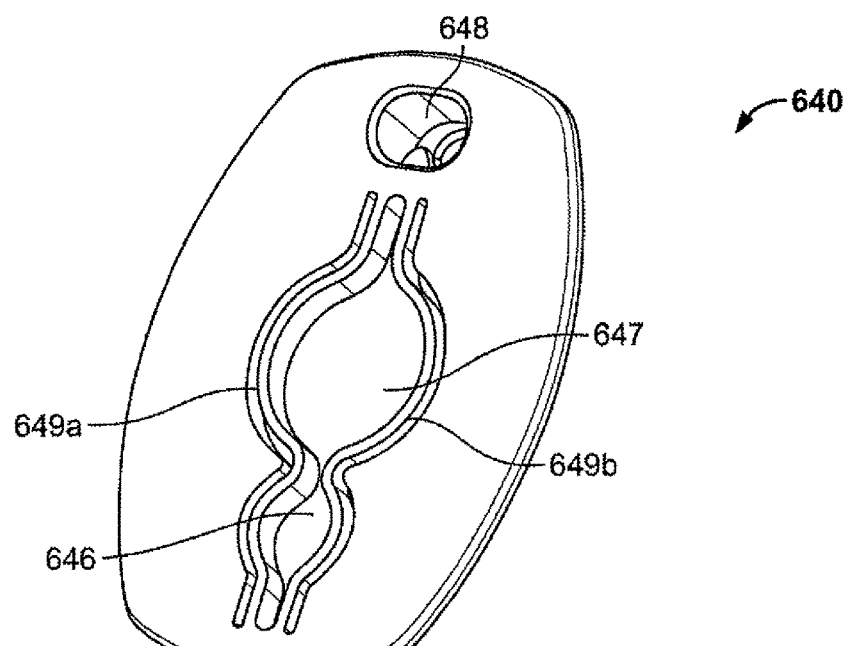
FIG. 9B is another perspective view of the humeral trial adaptor of FIG. 9A.

In order to account for the gap between implant head 525' and stem implant 500, for example, a humeral trial adaptor 640 as shown for example in FIGS. 9A and 9B is utilized. Trial adaptor 640 has a superior surface 641 and an inferior surface 642. Superior surface 641 and inferior surface 642 are preferably planar surfaces separated by linear distance D1. An engagement portion 643 protrudes inferiorly from inferior surface 642. Engagement portion 643 has a contact surface 644 in which a protrusion 645 protrudes outwardly from. Trial adaptor includes a first aperture 646, a second aperture 647 and a third aperture 648. Trial adaptor 640 further includes first and second flexible retaining portions 649a, 649b that extend along a length of both first and second apertures 646, 647.

Figure 10A:
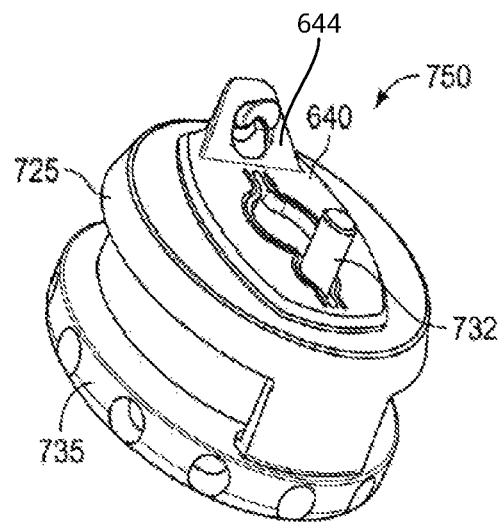
FIG. 10A is a perspective view of a trial assembly including the humeral trial adaptor of FIG. 9A coupled to one embodiment of a humeral trial cup coupled to a humeral trial insert.
Figure 10B:
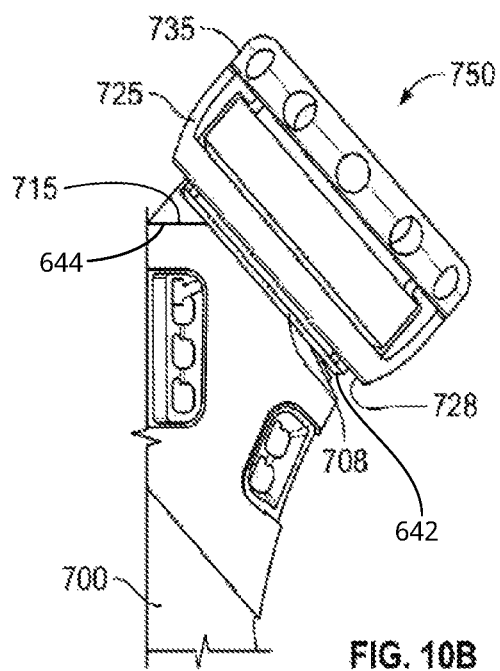
FIG. 10B is a front view of the trial assembly of FIG. 10A coupled to an exemplary trial or implant stem.

FIG. 10A is a perspective view of a trial assembly 750 including trial adaptor 640 coupled to one embodiment of a trial cup 725 coupled to a trial insert 735. Trial cup 725 includes a base surface 728 in which a first engagement portion 732 extends outwardly therefrom. When trial adaptor 640 is coupled to trial cup 725, first engagement portion 732 of trial cup 725 extends through first aperture 646. First and second flexible retaining portions 649a, 649b come in contact with an outer surface of first engagement portion 732 of trial cup 725 and help to retain the coupling between trial adaptor 640 and trial cup 725. As shown in FIG. 10B, trial assembly 750 is coupled to an exemplary trial or implant stem 700. In this embodiment, contact surface 644 of trial adaptor 640 is in contact with a second contact surface 715 of trial stem while inferior surface 642 is in contact with a first contact surface 708. Base surface 728 is separated from first contact surface 708 by linear distance D1.

In fracture or similar settings, trial adaptor 640 can therefore be used to account for the differences between the coupling of a trial cup or head with a trial or implant stem and an implant cup or head with an implant stem. During trialing, the surgeon or other operating room personal will use trial adaptor 640 along with a trial cup or head and a trial or implant stem which corresponds to a selected implant cup or head and the implant stem. FIGS. 11A-B are exemplary embodiments of humeral cup trial and head assemblies 850, 850'. FIG. 11A shows cup trial 825, trial adaptor 840 and stem implant 800 coupled to one another. A first engagement portion 832 of cup trial 825 extends through trial adaptor 840 and into a first catch aperture 812 while a second engagement portion 834 of cup trial 825 extends through trial adaptor 840 and into a second catch aperture 818. A base surface 828 of cup trial 825 is separated from a first contact surface 808 of stem implant by linear distance D1. FIG. 11B shows head trial 825', trial adaptor 840 and stem implant 800 coupled to one another. An engagement portion 833' of head trial 825' extends through trial adaptor 840 and into a trial recess 814 of stem implant. A base surface 828' of cup trial 825' is separated from a first contact surface 808 of stem implant by linear distance D1.

Figure 12A:
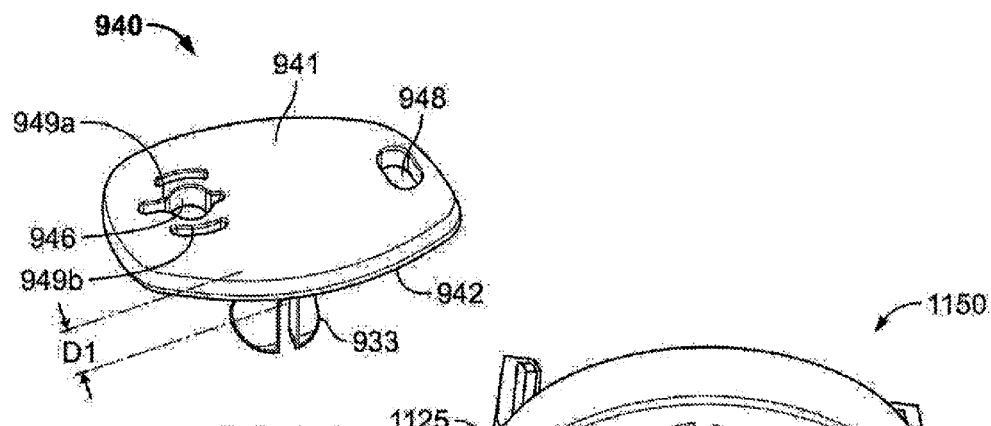
FIG. 12A is a perspective view of another embodiment of a humeral trial adaptor of the present invention.

FIG. 12A is a perspective view of another embodiment of a humeral trial adaptor 940 of the present invention. Trial adaptor 940 has a superior surface 941 and an inferior surface 942. Superior surface 941 and inferior surface 942 are preferably planar surfaces separated by linear distance D1. An engagement portion 933 protrudes inferiorly from inferior surface 942. Engagement portion 933 is adapted to be received, for example, in trial recess 814 of stem implant 800. Trial adaptor 940 includes a first aperture 946 and a third aperture 948. Trial adaptor 940 further includes first and second retaining portions 949a, 949b that extend along a length of first aperture 946.

Figure 12B:
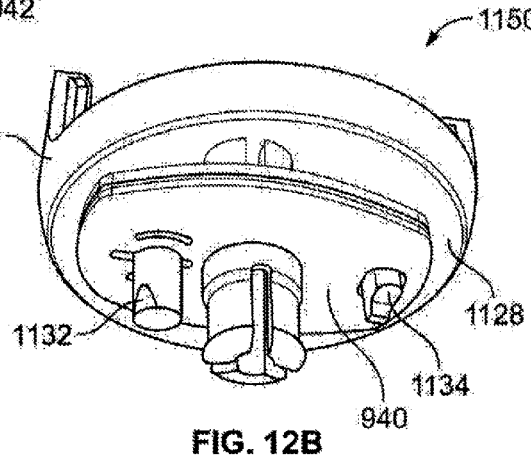
FIG. 12B is a perspective view of the humeral trial adaptor of FIG. 12A coupled to one embodiment of a humeral trial cup.

FIG. 12B is a perspective view of a trial assembly 1150 including the humeral trial adaptor 940 of FIG. 12A coupled to one embodiment of a humeral trial cup 1125. Trial cup 1125 includes a base surface 1128 in which a first engagement portion 1132 and a second engagement portion 1134 extending outwardly therefrom. When trial adaptor 940 is coupled to trial cup 1125, first engagement portion 1132 of trial cup 1125 extends through first aperture 946 while second engagement portion 1134 of trial cup 1125 extends through third aperture 1148. First and second retaining portions 949a, 949b come in contact with an outer surface of first engagement portion 1132 of trial cup 1125 and help to retain the coupling between trial adaptor 940 and trial cup 1125.

Figure 13A:
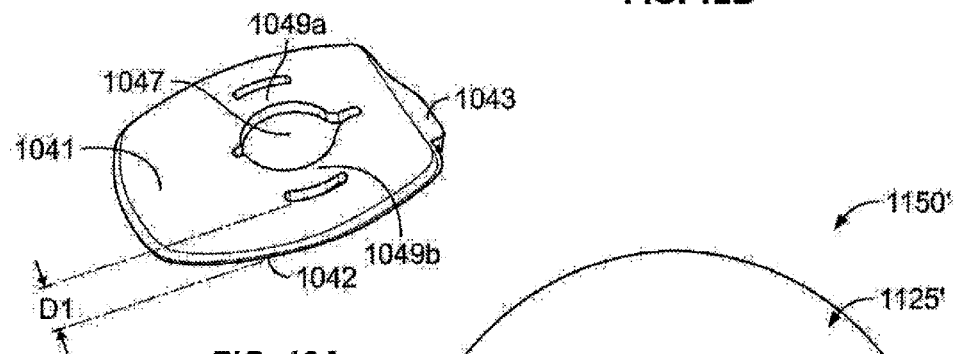
FIG. 13A is a perspective view of another embodiment of a humeral trial adaptor of the present invention.

FIG. 13A is a perspective view of another embodiment of a humeral trial adaptor 1040 of the present invention. Trial adaptor 1040 has a superior surface 1041 and an inferior surface 1042. Superior surface 1041 and inferior surface 1042 are preferably planar surfaces separated by linear distance D1. An engagement portion 1043 protrudes inferiorly from inferior surface 1042. Engagement portion 1043 has a contact surface 1044 adapted to come in contact with a corresponding surface of a trial stem. Trial adaptor 1040 includes a second aperture 1047 surrounded by first and second retaining portions 1049a, 1049b that extend along a length of second aperture 1047.

Figure 13B:
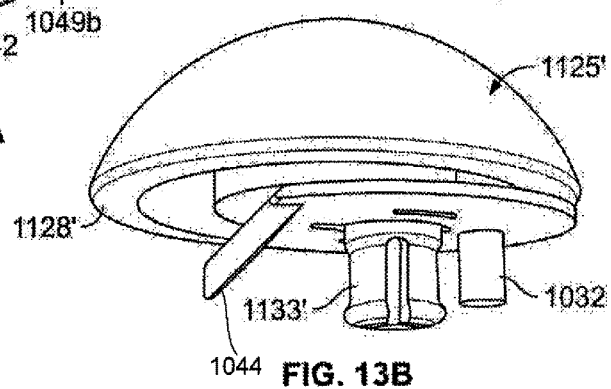
FIG. 13B is a perspective view of the humeral trial adaptor of FIG. 13A coupled to one embodiment of a humeral head trial.

FIG. 13B is a perspective view of a trial assembly 1150' including the humeral trial adaptor 1040 of FIG. 13A coupled to one embodiment of a humeral head trial 1125'. Head trial 1125' includes a base surface 1128' in which an engagement portion 1133' extends outwardly therefrom. Engagement portion 1133' of head trial 1125' extends through second aperture 1047 of trial adaptor 1040 and is adapted to be received, for example, into trial recess 814 of stem implant 800. First and second retaining portions 1049a, 1049b come in contact with an outer surface of engagement portion 1133' of head trial 1125' and help to retain the coupling between trial adaptor 1040 and head trial 1125'. A base surface 1128' of head trial 1125' is separated from a first contact surface 808 of stem implant 800 (not shown in FIG. 13B), for example, by linear distance D1. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopedic trialing system comprising:
    a stem including a shaft adapted to be received in a canal of a bone, the stem having a first planar surface and a second planar surface extending at a non-zero angle with respect to the first planar surface, the stem defining a first recess and a second recess;
    an adaptor including a top surface, a bottom surface contacting the first planar surface of the stem, an aperture extending through the top and bottom surfaces, an engagement member extending below the bottom surface and having a surface angled relative to the bottom surface the angled surface of the engagement member contacting the second planar surface of the stem, and the adaptor further including a protrusion; and
    a trial member having a contact surface and a protrusion extending through the aperture of the adaptor and at least partially into the first recess of the stem, and wherein the protrusion of the adaptor extends at least partially into the second recess to assist in coupling together the trial member, the adaptor and the stem.

2. The orthopedic trialing system of claim 1, wherein the top surface of the adaptor contacts and lies adjacent to the contact surface of the trial member when the trial member, the adaptor, and the stem are coupled together.

3. The orthopedic trialing system of claim 2, wherein each of the top and bottom surfaces of the adaptor and the contact surface of the trial member are planar.

4. The orthopedic trialing system of claim 1, wherein the stem defines a third recess.

5. The orthopedic trialing system of claim 1, wherein the stem is selected from the group consisting of a broach, a trial stem, and a prosthesis stem.

6. The orthopedic trialing system of claim 1, further comprising a flexible member disposed within the aperture of the adaptor for engaging the protrusion of the trial member.

7. An orthopedic trialing system comprising:
a stem including a shaft portion adapted to be received in a canal of a bone, the stem having a first planar surface, a second planar surface extending at a non-zero angle with respect to the first planar surface, and first and second recesses;
an adaptor having a thickness defined by a linear distance between top and bottom surfaces thereof, the bottom surface contacting the first planar surface of the stem, the adaptor including an aperture extending through the top and bottom surfaces, an engagement member extending below the bottom surface and having a surface angled relative to the bottom surface the angled surface of the engagement member contacting the second planar surface of the stem, and the adaptor further including a protrusion; and
a trial member having a planar surface and a protrusion, the protrusion of the trial member extending through the aperture of the adaptor and at least partially into the first recess of the stem, wherein the protrusion of the adaptor extends at least partially into the second recess to assist in coupling the stem, the adaptor, and the trial member together, whereby the planar surface of the stem and the planar surface of the trial member are separated by the thickness of the adaptor.

8. The orthopedic trialing system of claim 7, wherein the top surface of the adaptor contacts and lies adjacent to the planar surface of the trial member when the trial member, the adaptor, and the stem are coupled together.

9. The orthopedic trialing system of claim 8, wherein the top and bottom surfaces of the adaptor are planar.

10. The orthopedic trialing system of claim 7, wherein the stem is selected from the group consisting of a broach, a trial stem, and a prosthesis stem.

11. An orthopedic trialing system comprising:
a stem including a shaft portion adapted to be received in a canal of a bone, the stem defining first, second and third recesses, the third recess extending in a transverse direction relative to the first and second recesses;
an adaptor having top and bottom surfaces, a protrusion extending from the bottom surface and into the second recess of the stem, and first and second apertures extending through the top and bottom surfaces; and
a trial member having a first protrusion extending through the first aperture of the adaptor and at least partially into the first recess of the stem, and a second protrusion having an angled end extending through the second aperture of the adaptor and at least partially into the third recess of the stem coupling together the trial member, the adaptor and the stem.

* * * * *